(12) United States Patent
Koruga (10) Patent No.: US 8,058,483 B2
(45) Date of Patent: Nov. 15, 2011

(54) COMPOSITION OF MATTER CONTAINING HARMONIZED HYDROXYL MODIFIED FULLERENE SUBSTANCE

(75) Inventor: Djuro Koruga, Beograd (RS)

(73) Assignee: DVB Global, Lincolnwood, IL (US)

( * ) Notice: Subject to any disclaimer, the term of this patent is extended or adjusted under 35 U.S.C. 154(b) by 955 days.

(21) Appl. No.: 12/025,659

(22) Filed: Feb. 4, 2008

(65) Prior Publication Data

US 2008/0188415 A1    Aug. 7, 2008

Related U.S. Application Data

(60) Provisional application No. 60/899,140, filed on Feb. 2, 2007, provisional application No. 60/959,431, filed on Jul. 13, 2007.

(51) Int. Cl.
| | |
|---|---|
| *C07C 35/00* | (2006.01) |
| *A61K 38/16* | (2006.01) |
| *A61K 47/08* | (2006.01) |

(52) U.S. Cl. .......... 568/700; 514/772; 424/489
(58) Field of Classification Search ........... 568/700; 514/772; 424/489
See application file for complete search history.

(56) References Cited

U.S. PATENT DOCUMENTS 5,177,248 A * 1/1993 Chiang et al. ............ 560/86
5,648,523 A * 7/1997 Chiang ................... 562/100

\* cited by examiner

*Primary Examiner* — Sikarl Witherspoon
(74) *Attorney, Agent, or Firm* — Rockey, Depke & Lyons, LLC; Joseph A. Fuchs

(57) ABSTRACT

The present invention provides a composition of matter having a harmonized form $(\Phi/\phi)$ of a hydroxyl modified fullerene having a molecular formula of $C_{60}(OH)xH_y\forall_z$ (where x is from 10 to 36, and y is from 0 to 24 and z is from 0 to 12) the composition of matter having substantially the same $^{13}C$ NMR spectra shown in FIG. 8 having a dominant peak at 170.2 ppm. This peak shows that each carbon atom of $C_{60}$ is equally covered by OH groups and that the system $[C_{60}(OH)xH_y\forall_z]^{(\Phi/\phi)}$ is one body entity.

19 Claims, 5 Drawing Sheets

COMPOSITION OF MATTER CONTAINING HARMONIZED HYDROXYL MODIFIED FULLERENE SUBSTANCE

CROSS-REFERENCE TO RELATED APPLICATION

This application claims priority to U.S. Provisional Patent Application No. 60/899,140 filed on Feb. 2, 2007 and U.S. Provisional Patent Application No. 60/959,413 filed Jul. 13, 2007 each of which are incorporated herein by reference and made a part hereof.

FEDERALLY SPONSORED RESEARCH OR DEVELOPMENT

Not Applicable.

BACKGROUND OF THE INVENTION

1. Technical Field

The present invention provides harmonized hydroxyl-modified fullerenes, hydroxyl-modified fullerenes in a suitable carrier, and hydroxyl-modified fullerene formulations including a suitable carrier with optional additives. These compositions of matter and formulations have numerous applications including, for example, the cosmetic and healthcare fields. What is meant by the term "harmonized" is that ratio of two quantities obeys the golden mean ratio. Examples include the energy states of atoms or molecules; the length of covalent, ionic, hydrogen or other type of bonds; electrical field strengths, and magnetic field strengths to name a few.

2. Background Art

Schrödinger's book *What is Life?* has had an enormous influence on the development of molecular biology, stimulating scientists such as Crick and Watson to explore the double helix structure of DNA as the basis of life (Schrödinger 1943, Watson and Crick, 1953). One of the central points in the book is statement "that the most essential part of a living cell—the chromosome fiber—may suitably be called an aperiodic crystal" as opposed to a periodic crystal in classical physics. It has been found that DNA works as a classical information system based on a double helix structure and a ternary coding system with $4^3=64$ coding words [Crick, 1963]. Many years later it was recognized that that the genetic ternary code, which codes for amino and imino acids in proteins, also, may be represented as a classical binary code $2^6=64$ [Swanson, 1984, Doolittle, 1981, Rakočević, 1998].

The importance of hydrogen bonding in the structure and function of biological macromolecules was predicted by the earliest investigators (Pauling, Corey, and Branson, 1951). According to Linus Pauling, the first prediction of the existence of a hydrogen bond should be attributed to M. L. Huggins in 1919 and independently to W. M. Latimir and W. H. Rodebush in 1920. Bearing in mind that most biological systems contain water from 60% to 80%, the importance of hydrogen bonds has become most relevant for understanding how biomolecular machinery, as a complex system, works. Within a collection of water molecules, the hydrogen atom is covalently bound to an oxygen atom in the water molecule and hydrogen bonds with oxygen atoms on separate water molecules. It is well known that covalent bond may only be described by quantum mechanics, because each electron does not really belong to a single atom—it belongs to both simultaneously. For a long period of time, scientists believed that the hydrogen bond could be perfectly understood by the principles of electrostatic interactions using Coulomb's law (pre-$20^{th}$ century classical physics), based on the attraction and repulsion between charged particles separated from each other by a distance. However, recent experimental data indicate that a hydrogen bond has double identity: classical and quantum (Isaacs, 1999, Barbiellini, and Shukla, 2003). This is the key point for understanding a new approach to explaining bow DNA and proteins function in water. It is believed that water itself may be a coding structure, via its hydrogen bonds, if some water molecules are organized in clusters and some of them are ordered in interconnected chains between water clusters by Fibonacci law. Some local domains of water, under the influence of DNA and microtubules, may be responsible for organizing water molecules into clusters as complementary coding forms. In a human, 40% of it is water is free water, while 60% is captured by biomolecules. Estimates predict that only 5% of free water is in clusters organized by a sphere packing law of coding number 12. The remaining 95% of free water is in the form of "chaos" with local polymerized islands.

According to a coding approach based on sphere packing analysis, the optimal molecular organization of water molecules should be as a hydrogen-bonded $(H_2O)_n$ polyhedra $5^{12}6^n$ (n=0,2,4 . . . ), where $5^{12}$ represents 12 pentagons and n different number of hexagons (Jeffrey, 1997). Through hydrogen bonds dynamics, this polyhedra-shaped structure of water molecules posses a spherical coding system $2^5=32$. The arrangement of water molecules, based on number 12, may represent a coding system which is part of an optimal information peak of sphere packing (Sloane 1984, Koruga, 1986). Accordingly, water hydrogen-bonded polyhedra is both compatible and complementary with the coding system of the genetic code (DNA and proteins).

An understanding of the hydrogen bonding dynamic on quantum chemical scales is useful in the study of biological systems, including the study of diseases such as cancer and medical and cosmetic conditions related to the human skin. By way of background with regard to the human skin, the epidermis is a dynamic renewing structure that provides life-sustaining protection from the environment. Keratinocytes and melanocytes are the major cells types responsible for the structure of the epidermis. They begin as stem cells in the basal epidermal layer. As keratinocytes move to the epidermal surface, the cells cease cell division and undergo morphological changes to form the prickle or spinous cells, granular cells, transition cells, keratinized squames and surface squames. One melanocyte cell may overlap a few keratinocytes giving them melanin (mechanism is yet unknown), which is responsible for protection of the environmental electromagnetic radiation (UV radiation) and neutralization of free radicals (Varni et al, 2004 van den Bossche, at al. 2006).

It is also well known that vitamin C (L-ascorbic acid) can be used in the treatment of conditions related to the skin. One of the major roles of vitamin C is its stimulation effects on collagen synthesis without affecting other protein synthesis. Vitamin C is a desired component of cosmetic products for both praline and lysine hydroxylase which stabilize the collagen molecule. This reaction is necessary for skin to maintain its strength.

Also, collagen distortion below the base level membrane (lamina fibroreticularis) occurs when cancer penetrates through the epidermis into the dermis, and "opens the door" for metastases. From a classical communication channels point of view, gene expression is responsible for it: normal collagen, type I [$\alpha 1(I)_2\alpha 2(I)$], comprises two procollagen chains, the first $\alpha 1(I)$ (gene located on chromosome 17 (q21-q22)), and the second procollagen chain $\alpha 2(I)$ (gene located on chromosome 7(q21-q22)). According to quantum theory, quantum communication channels exists among keratinocyte or melanocyte and fibroblast cells (entanglement) based on hydrogen bonding in the DNA. When symmetry-breaking of hydrogen bonds happens in DNA, then automatically, through DNA-microtubule-water coding entanglement, synergy of classical and quantum communication is broken. There is experimental evidence that fibroblast cells and human melanoma cells interact with tumour cell growth as a function of tumour progression (Coinil, at.al. 1991). If UV radiation damages DNA on chromosome 7, in keratinocyte or melanocyte cells, then through non-classical quantum channels this information will transfer to both centriole (damaged cell) and fibroblast cells in the region. The centriole will become "wild" (from bipolar mitosis change to three polar or multipolar mitosis) and will start to divide chromosomes irregularly. The nucleus of an initial cancer cell will grow faster than normal cells. The "wild" cell will be duplicated and rapidly increase in number because positive feedback control mechanism water-centriole will change perpendicularly to centriole pairs (Koruga, et.al. 1992). From another side, fibroblast cells will cease synthesizing collagen α2(I). In the absence of α2(I), procollagen chains during assembly into procollagen molecules, will incorporate an additional α1(I) procollagen chain. This will give collagen type I-trimer with a structure [α1(I)$_3$]. The I-trimer links between procollagen chains do not fit well, and OH groups will be removed from collagen to make free water molecules. The volume of free water will increase from 20% in tissue (Foster and Schwan, 1986). A similar occurrence is observed in skin aging an accounts for the reason for people of advancing age frequently having cancer (Richard, at.al., 2004).

When this type of collagen becomes dominant in a given tissue, the lamina fibroreticularis (as "a woof" of basal lamina) becomes weak, because the interconnection between procollagen chains in procollagen molecules, based on hydrogen bonds, is not adequate (the electromagnetic shield of a basal membrane has holes). Then, a mass of skin cancer or melanoma, can penetrate the basal lamina and reach the superficial arteriovenous plexus (Brinkley, 2001).

Hydrogen bonding in biomolecule networks in cell and tissue, as well as their complex intermolecular connections, resemble spider webs. It is a link between classical and quantum behaviour of matter on molecular level, and it is a basic element of synergy between mass-energy and information in living matter.

DNA is coded by 4$^{th}$ perfect number code $2^n(2^{n+1}-1)$ with 8128 code words, which is responsible for protein coding (classical) and system complexity coding (quantum) by entanglement (Koruga, 2005, Koruga, et al. 2006). There is mapping one-to-one from genetic code to proteins by synergetic code. There is synergetic code (classical/quantum) in protein chain based on amino acids and peptide plains. Hydrogen bonds are links between classical and quantum behaviours of matter on a molecular level, and it is a basic element for synergy of mass-energy-information in living matter.

Understanding DNA as synergetic classical/quantum device, based on golden mean and the forth prefect number, may help us not only for better understanding of the origin of life, but also for finding methods for prevention and healing the most illnesses. Bearing in mind that proteins are the second side of DNA code, interaction and communication DNA-protein may be both through separate classical and quantum communications channels, and through synergetic one. However, synergetic approach, which we proposed open a new possibilities for therapy of many skin illnesses including cancer.

DNA and water exist in a very delicate relationship. In normal situations, DNA operates in accordance with the forth perfect number law, while water operates in accordance with the third perfect number law. In normal situations, the DNA-water system works harmonically. However, when, for some reason, DNA collapses from operating in accordance with the fourth perfect number law to the third perfect number law, then information about the disharmonic state of DNA travels more smoothly through water than its harmonic one.

These and other aspects and attributes of the present invention will be discussed with reference to the following drawings and accompanying specification

BRIEF DESCRIPTION OF THE DRAWINGS

FIG. 4 is a diagrammatic view of a hydroxyl-modified fullerene scavenging a water molecule to return the protein to a healthy state shown in FIG. 3a;

FIG. 5 is a diagram of a cluster of water molecules showing that the ratio of the length of an O—H covalent bond to the length of a hydrogen bond obeys the golden ratio;

FIG. 6a is a diagrammatic representation of a cluster of electrons in the ground state;

FIG. 6b is a diagrammatic representation of the cluster of electrons in an excited state resulting from applying energy to the electron cluster shown in FIG. 6a;

FIG. 6c is a diagrammatic representation of an electron cloud in an excited state forming a sunflower pattern as a result of subjecting the electron cluster of FIG. 6a to a harmonization process;

DETAILED DESCRIPTION OF THE INVENTION

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

Figures 1A, 1B:
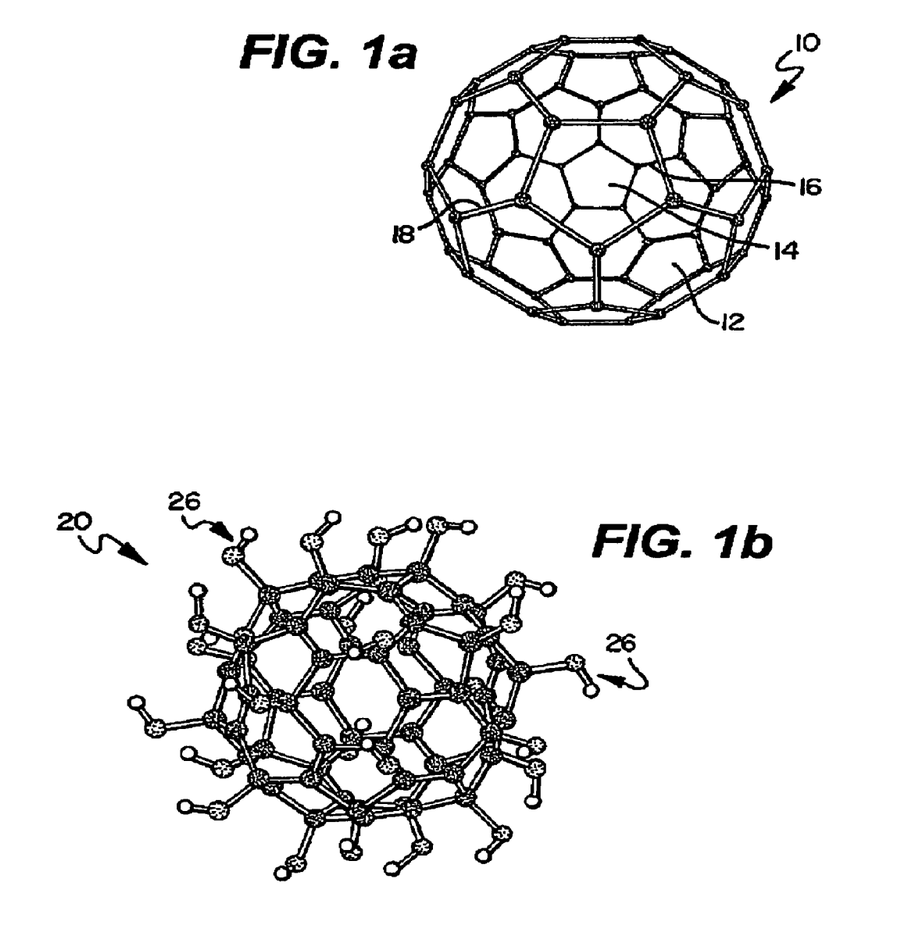
FIG. 1a is a diagrammatic view of a $C_{60}$ fullerene molecule.
FIG. 1b is a diagrammatic view of a $C_{60}(OH)_{24}$ molecule.

FIG. 1 a shows a $C_{60}$ fullerene 10 composed entirely of carbon atoms in the form of a hollow sphere in the shape of the familiar black and white soccer ball (Telestar 1970). Fullerenes comprise a family of carbon allotropes containing from 20 to 1000 or more carbon atoms in each cage-like structure. The structure of $C_{60}$ fullerene is a truncated icosahedron having 20 hexagon faces 12, 12 pentagon faces 14, all single bonds along pentagon perimeters 16, one double bond 18 and 2 single bonds per carbon. The $C_{60}$ has two bond lengths. A first bond length is along the edges of two hexagons and the second bond length is between the edge of a hexagon and a pentagon, the first bond length being greater than the second bond length. One of the crucial properties of the fullerene $C_{60}$ is the energy states of $T_{1g}$, $T_{2g}$, $T_{1u}$ and $T_{2u}$ for symmetry elements $C_5$, $C_5^2$, $S_{10}$ and $S_{10}^3$ are consistent with the golden mean. (Koruga, et.al., 1993, Dreselhaus, et al., 1996). Since, the symmetry properties of the structure is determinate of its vibration and rotation energy states, it has been shown that integral energy (translational, vibrational, rotational and electronic) states of fallerene $C_{60}$ follows the golden mean rule or ratio (Harter, 1989).

Figure 2:
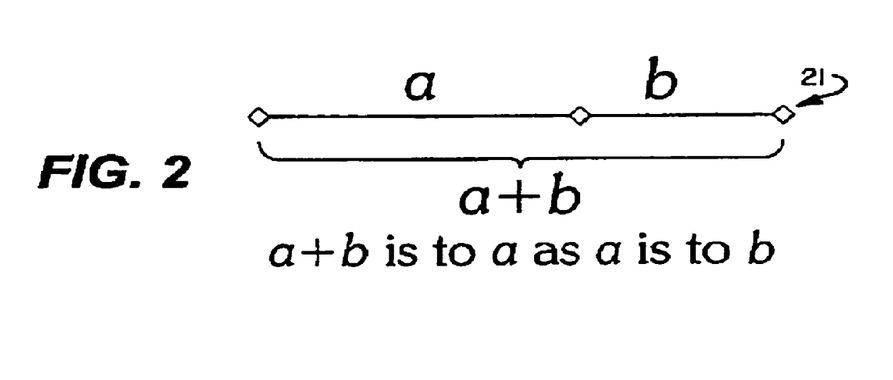
FIG. 2 is a diagrammatic representation of a Golden Mean Rule in one dimension.

FIG. 2 shows a figural representation 21 of the golden mean rule or golden ratio. The golden ratio usually designated with the symbol Φ and expresses the relationship that the sum of two quantities is to the larger quantify as the larger quantify is to the smaller quantity, that is a+b is to a as a is to b. The golden ratio can be expressed mathematically as:

$$\Phi = \pm(1+\sqrt{5})/2 \approx \pm 1.618033$$

The conjugate golden ratio $\phi = \pm 1/\Phi \approx \pm 0.618$ corresponds to the length ratio taken in reverse order b/a.

In a preferred form of the invention, FIG. 1b shows fullerenes modified 20 with multiple hydroxyl groups $(OH)_x$ 26, multiple hydrogen atoms $(H_y)$, and/or molecules with one or more molecules with hydroxyl groups $\forall_z$ to form substances $C_{60}(OH)xH_y\forall_z$ (where x is from 10 to 36, and y from 0 to 24 and z from 0 to 12). These compounds will be referred to herein as Modified Fullerenes 24. Modified Fullerenes are soluble in water and interact with water via hydrogen bonds. Modified Fullerenes are susceptible to degradation from environmental and chemical attacks. Such exposure to environmental and chemical agents can lead to a removal of functional groups from the Modified Fullerene. This is undesirable as unmodified or "naked" fullerenes $C_{60}$ have been found to be cytotoxic.

Experiments with $C_{60}(OH)_{24}$ 20 (FIG. 1b) in two different human cell lines show that the cytotoxicity is a sensitive function of surface derivatization (Sayes, 2004). Experiments strongly suggest that the mechanism of cell death is oxygen radical induced peroxidation of the lipid bilayers of cells by "naked" nano-$C_{60}$. In experiment with human dermal fibroblasts, human liver carcinoma cells (HepG2), and neuronal human astrocytes at doses higher than 50 ppb ($LC_{50}$=2-50 ppb, depending on cell type) cytotoxicity arise after 48 h of exposure (Sayes, 2004). However, in the same experiments it was shown Modified Fullerenes 20, show no cytotoxicity. Thus, it is an important aspect of the present invention to provide a stable Modified Fullerene.

Toxicity test for harmonized, Modified Fullerenes has shown this substance is not cytotoxic when the material is subjected to a *Salmonella typhimurium* reverse mutation assay (AMES test). The Ames test is used to determine any potential mutagenic activity of the test HMF material. The HMF material was exposed to a large number of test organism in an agar plate. The agar plates were monitored for growth of revertants (organisms mutating to the wild type). The number of wild type organisms are counted to estimate the mutagenic potential of the HMF material. The tests results showed the HMF material was not mutagenic.

It has been found by the present inventor, the Modified Fullerenes can be stabilized in a harmonization process. Modified Fullerenes, are made by a procedure described in U.S. Pat. No. 5,648,523 which is incorporated herein by reference in its entirety by reference and made a part hereof. More particularly, Modified Fullerenes can be prepared by one of the following six methods. First, Modified Fullerene can be prepared from hydrolysis of the reaction products of fullerenes, either pure $C_{60}$ or a mixture of $C_{60}$ (84%) and $C_{70}$ (16%), with nitronium tetrafluoroborate in the presence of organocarboxylic acid ($RCO_2H$) at ambient temperature. Chiang, et al., U.S. Pat. Nos. 5,177,248; et al. 5,294,732; and et al., J. Am. Chem. Soc. 1992, 114, 10154; Chiang, et al., J. Am. Chem. Soc. 1993, 115, 5453. The structure of the resultant Modified Fullerene has been characterized to consist of $C_{60}O_x(OH)_y$, with x<5 and y=18 on average.

Second, a Modified Fullerene can be synthesized via hydrolysis of the reaction products of fullerenes, either pure $C_{60}$ or a mixture of $C_{60}$ (85%) and $C_{70}$ (16%), with a solution of sulfur trioxide (30%) in sulfuric acid. See Chiang, et al., J. Org. Chem. 1994, 59, 3960. The structure of the resultant Modified Fullerene has been characterized to consist of $C_{60}(OH)_y$, with y=12 on average.

Third, a Modified Fullerene can be prepared by the reaction of fullerenes with either a mixture of conc. $H_2SO_4$, conc. $HNO_3$ and water at 90° C. or a mixture of oleum ($H_2SO_4$—$SO_3$), $KNO_2$ and water. See Chiang, et al., U.S. Pat. Nos. 5,177,248; 5,294,732; J. Chem. Soc., Chem. Commun. 1992, 1791; Chiang, et al., Mat. Res. Soc. Symp. Proc. 1992, 247. The structure of the resultant Modified Fullerene has been characterized to consist of $C_{60}O_x(OH)_y$, with x<5 and y=15 on average.

Fourth, a Modified Fullerene can be synthesized by the reaction of fullerenes, dissolved in either benzene or toluene, with aqueous sodium hydroxide in the presence of a catalytic amount of tetrabutylammonium hydroxide and oxygen (in air). See Li, et al., J. Chem. Soc., Chem. Commun. 1993, 1784. The structure of the resultant Modified Fullerene has been characterized to consist of polyhydroxylated $C_{60}$ fullerene derivatives with 26 hydroxy groups per $C_{60}$ cage on average.

Fifth, a Modified Fullerene can be prepared by the reaction of fullerenes, dissolved in either benzene or toluene, and gaseous nitrogen dioxide, followed by hydrolysis of resulting products with aqueous NaOH. See Chiang, et al., Tetrahedron, "Efficient Own-Flask Synthesis of Water-soluble Fullerenols." Gaseous nitrogen dioxide can be generated by either reacting $NaNO_2$ with $FeSO_4$ in aqueous $H_2SO_4$ in the presence of air (Roy, et al., J. Chem. Soc., Chem. Commun. 1994, 275) or reacting $NaNO_2$ with conc. $HNO_3$. The former method yields nitrofullerenols consisting of 6-8 nitro and 7-12 hydroxyl groups per $C_{60}$. Hydrolysis of these products results in Modified Fullerenes with 13-20 hydroxy groups per $C_{60}$. The later method gives water-soluble Modified Fullerenes with a maximum number of hydroxyl groups per $C_{60}$ as 20 as identified by the FAB mass spectroscopy.

Sixth, a Modified Fullerene can be synthesized by the reaction of fullerenes with an excess of $BH_3$-tetrahydrofuran (THF) complex followed by hydrolysis with either sodium hydroxide/hydrogen peroxide or sodium hydroxide. See Schneider, et al., J. Chem. Soc., Chem. Commun. 1994, 463.

Harmonizing the Modified Fullerene

To stabilize the Modified Fullerenes to withstand chemical and environmental attacks to avoid stripping of their functional groups, the Modified Fullerenes are subjected to a harmonization procedure. The harmonization procedure promotes the electron energy levels of the molecular orbitals of the O13 H covalent bonds from a ground state (FIG. 6a) up one energy level to a harmonized state (FIG. 6c) where the valence electrons 50 are at a greater distance away from the nucleus than when in the ground state. This creates larger distances between bonding sites on the spherical surface of the Modified Fullerene of hydrogen electrons of x and y groups, forming a dynamical, non-localized cloud "Θ cloud" 84 (FIG. 9) of electrons capable of forming a hydrogen bonding network. In one preferred form of the invention, energy state of the Θcloud assumes the shape of a "sunflower" pattern 52.

Figure 6:
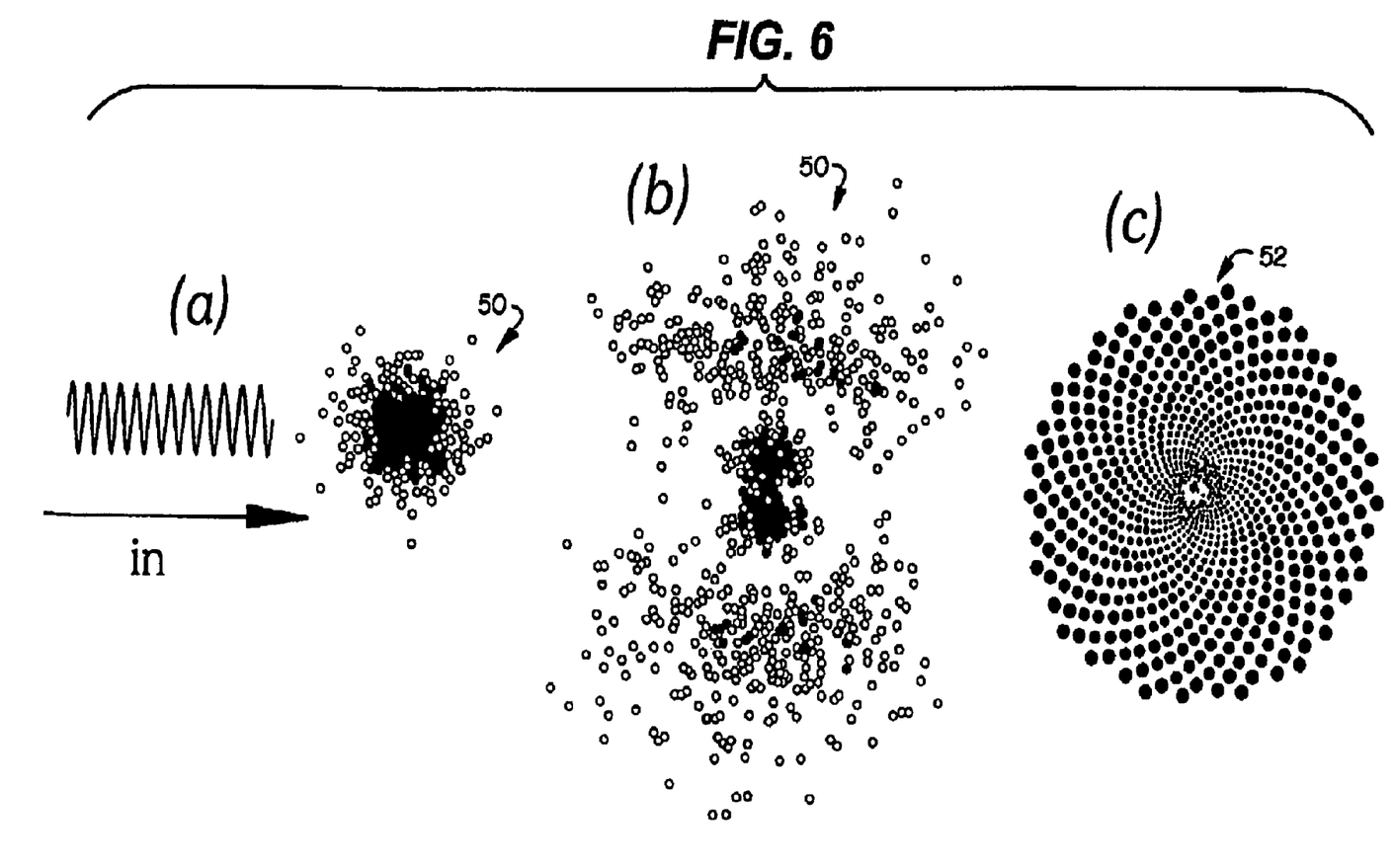

FIGS. 6*a-c* shows the electron cloud of a hydrogen atom in three different states. FIG. 6*a* shows the electron cloud in a ground, unexcited, state. FIG. 6*b* shows the same electron cloud when exposed to random radiation showing the electrons in an excited state resulting with a substantial portion of the electrons in positions farther from the nucleus when compared to the electrons in the ground state. FIG. 6*c* shows the electron cloud of hydrogen atoms exposed to harmonized excitation energy ($E^{\Phi/\phi}$) as opposed to random radiation. The sunflower shaped Θcloud 84 allows for hydrogen atoms to hydrogen bond to oxygen atom wherein the hydrogen bond the length of the O—H covalent bond and the length of the O—H—H hydrogen bond length obey the golden ratio shown in FIGS. 2 and 5 and described above.

Prior to 1999, the standard teaching stated that hydrogen bonds existed between water molecules because of the electrical attractions between a positively charged hydrogen atom and a negatively charged oxygen atom in a neighboring molecule. These electrostatic interactions can be explained perfectly by classical physics—Coulomb's law, by which it is possible to describe the attraction and repulsion between charged particles separated from each other by a distance. Experiments carried out 1999 clearly showed that electrons, like all other objects in nature, naturally seek their lowest energy state, through minimization of their total energy (including their energy of motion). Lowering an electron's kinetic energy means reducing its velocity and momentum. According to the Heisenberg Uncertainty Principle, by reducing the momentum of electrons the electrons must spread out in space thereby delocalizing the electrons into a semi-π electron cloud 84 (Θ cloud). In other words, the electrons in the hydrogen bond are quantum mechanically shared with more than one bonding site. Isaacs' experiment provides unambiguous evidence of the possible existence of multi-bonding hydrogen electrons in hydrogen bonds. Recent studies of hydrogen bonding in water, using very fast multi-dimensional nonlinear infrared spectroscopy, shows that hydrogen-bonded network of liquid water has an energy redistribution on a femtosecond timescale (Cowan, 2005). Those experiments prove that multi-bonding hydrogen electrons exist and play an important role in hydrogen bond network of matter.

The hydrogen atom is the simplest case of positive/negative charge organization in a spherical shape because it has a nucleus of one proton and one electron orbiting the nucleus. The electron has a certain total energy; the essence of quantum theory is that electrons remain in stable states of specific energies, and for each state there is a particular orbit. When an electron is in the lowest energy level, called the ground state, its radius is 52.9 pm. The electron must gain energy to move out to larger orbits. The orbits, and so the energy levels, follow strict spacing rules determined by quantum physics. Energy can be added to the atom either by collision with another particle or by absorption of a photon with sufficient energy. When the electron jumps up one or more energy levels the hydrogen is said to be in an excited state with an orbital radius of 236.8 pm for level two and 473.0 pm for level three (Lyman series). In normal conditions, electrons remain in an excited state for a very short period of time and drop to a lower level in about $10^{-8}$ seconds (Balmar series), emitting a photon with energy equal to the difference in the energy of the excited level to the level to which it drops. A hydrogen atom is in state one (ground state) as a gas $H_2$ or in an inorganic compound. However, hydrogen atoms in biomolecules and biological water are mostly in state two. Hydrogen ions in water have a quasi-proton existence because the proton never exists in aqueous solution as a free ion; it is always hydrated by being associated with neighboring water molecules. A proton in aqueous solution is very mobile, hopping from one water molecule to another with a period of about $10^{-15}$ second.

The potential importance of hydrogen bonding in the structure and function of biomolecules was predicted by Pauling and Corey (1951), Watson and Crick (1953) and numerous other scientists. Hydrogen bond energies can vary in strength depending on numerous factors and can have values of 15-40 kcal/mol, 4-15 kcal/mol and 1-4 kcal/mol for strong bonds, moderate bonds and weak bonds, respectively. Intermolecular hydrogen bonds have force constant from 60 N/m to 120 N/m. In a preferred form of the present invention, hydrogen bonds will be of moderate strength with a force constant of about 80 N/m and energies 4-15 kcal/mol. Such moderate hydrogen bond strengths correspond to a hydrogen bonding structure having a distance from a center of a donor atom to a center of an acceptor atom of about 280±10 pm.

It is well known that hydrogen-bonding 32 exists in functional groups 33 in protein side chains 34 (See FIG. 3*a*, healthy hydrogen bonding) such as in: lysine-histidine or tryptophan, arginine-glutamic acid or asparagic acid, tryptophan or praline, or histidine-tyrosine or threonine or serine in a donor-acceptor interaction. In protein and nucleic acid structures the distance from the center of a donor atom to the center of an acceptor atom is 290±10 pm and 310±20 pm, respectively. However, this intramolecular hydrogen bonding in functional groups of proteins is dynamic in nature with neighboring water molecules "competing" to take a donor or acceptor position normally occupied by an atom in the protein. In some cases, under the influence of external or internal factors, a water molecule 37 may occupy the position of a natural, intramolecular, hydrogen bond 38 in proteins (FIG. 3*b*, unhealthy hydrogen bonding), changing the conformation of the protein and its functional characteristics.

Figure 3:
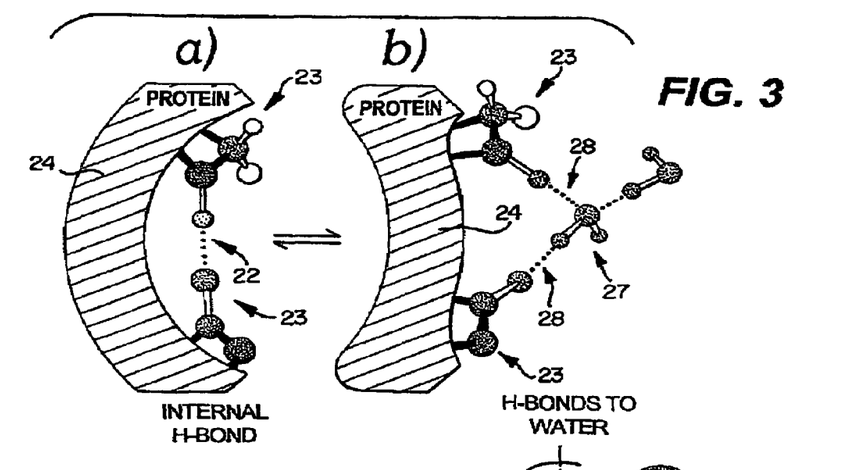
FIG. 3a is a diagrammatic view of general internal hydrogen bonding in a protein (healthy bonding)
FIG. 3b is a diagrammatic view of external hydrogen bonding in a protein (unhealthy bonding)
Figures 4, 5:
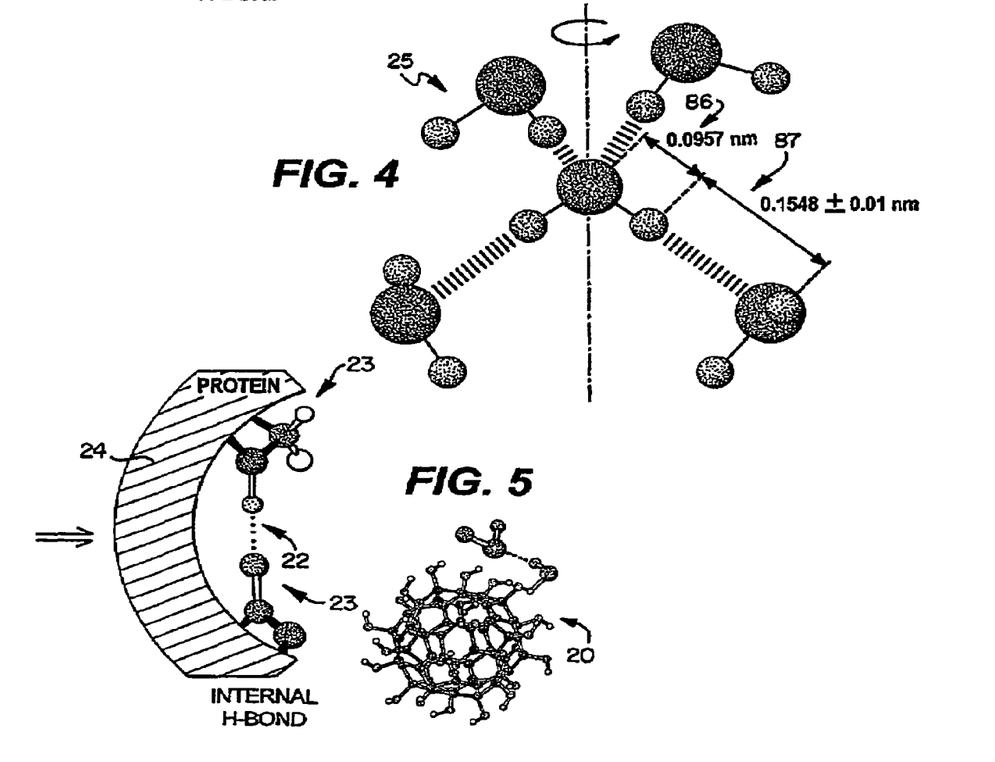

We have identified a direct correlation between the energy levels of the unhealthy hydrogen bonding to the structural intramolecular integrity of biomolecules (e.g., protein, DNA, among others). We further identified that a bio-molecule (e.g., protein, DNA, among others) is "healthy" (FIG. 3*a*) (i.e., having normal and natural functionality with constituent molecules at the intrinsic global energy level possible for that biomolecule) when water molecules interact and are connected to the biomolecules via weak bonds. In this healthy state the biomolecule operates at its optimal and most efficient state, maximizing proper functional interaction with other biomolecules (e.g., between different pro-collagen biomolecules which gives collagen fibers its structure) and efficient interaction with the molecular system as a whole. We have also observed that biomolecules, that are healthy, have a different structural confirmation state from that observed in "unhealthy" biomolecules (FIG. 3*b*). Additionally, we discovered that through external influence, a non-healthy biomolecule can adopt the structural confirmation of that observed in a healthy biomolecule (FIG. 4). This structural confirmation state change, in-turn, helps attract and develop non-covalent bonds with adjacent water molecule(s) and adjacent hydroxyl group(s) (OH), helping the previously "unhealthy" biomolecule to return to good health. This confirmation change for unhealthy biomolecules can be achieved by exposing the unhealthy biomolecule to an externally induced excitation frequency with a wave number between 500 to 3800 $cm^{-1}$.

Figure 9:
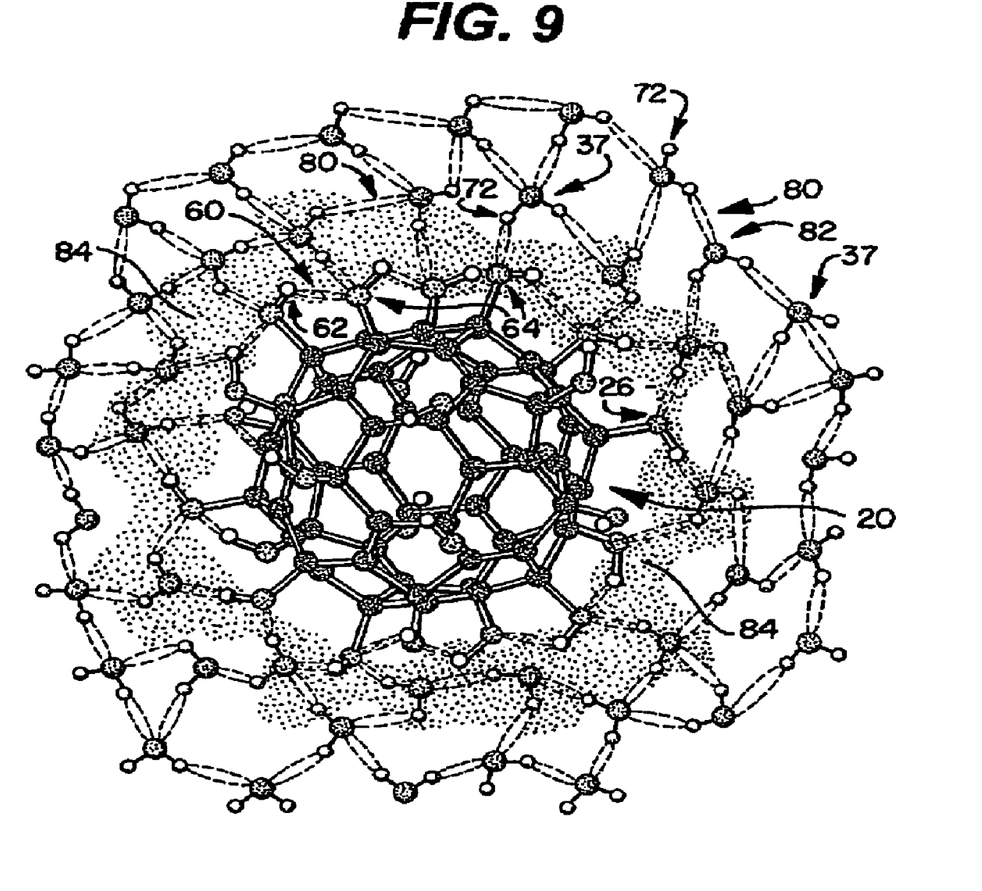
FIG. 9 is a diagrammatic view of a $C_{60}(OH)_{24}$ in water showing three levels of hydrogen bonding.

One suitable source of the externally induced excitation energy having a wave number between 500 to 3800 $cm^{-1}$ can be provided by exposure of the unhealthy biomolecule to a harmonized Modified Fullerene 20 as shown in FIGS. 4 and 9. The harmonized Modified Fullerene 20 influences and enables the unhealthy biomolecule to attract and develop a non-covalent bond with adjacent water molecule(s) and adjacent hydroxyl group(s) (OH). This leads to the biomolecule "self-repairing" itself and returning to good "health" leading to beneficial health outcomes. The energy state (T1g, T2g, T1u and T2u) of the harmonized Modified Fullerene product provides the necessary excitation frequency with a wave number from 500 to 3800 cm−1.

The harmonization procedure requires forming a solution of the Modified Fulierenes and exposing the solution to polarized light, heating and a pulsing magnetic field. More particularly, solutions of Modified Fullerene are formed by dissolving the Modified Fullerene into an aqueous solution or other solubilizing agent. These solutions are optionally subjected to ultrasonication for 10 to 30 minutes. The Modified Fullerene-containing solution is then treated by exposure for a period of 0.5 hours to 2 hours simultaneously to: (1) a pulsing polarized light where the power source pulses from 20 W to 500 W in accordance with the (Fibonacci series "φ"), from a distance of 10 cm to 60 cm, and with a wave length of 320 nm to 4200 nm; (2) heating the solution while continuously stirring from 20° C. to 80° C. for ⅓ of the treatment time period followed by cooling the solution from 80° C. to 15° C. for ⅔ of the treatment time period; and (3) subjecting the solution to an oscillatory (Fibonacci series "Φ") magnetic field intensity from 0.4 T to 1.2 T. This procedure can be conducted in a "PHM system" (Photo-Heath-Magnet Devices) where solutions of volumes from 0.2-3 liters can be treated.

According to this procedure, the Θcloud 84 of temporally delocalized electrons of the hydrogen bonds of the now harmonized Modified Fullerene move around the surface of the harmonized Modified Fullerene forming a magnetic shield 84 (FIG. 9) (nano-magetosphere) having an intensity from 0.5 nT to 25 nT, the intensity oscillating in accordance with the golden mean law. If some molecules with positive or negative charges try to "attack" the harmonized Modified Fullerene they will glide behind the nano-magnetosphere, somewhat like how charged particles from outer space glide over the Earth's magnetosphere. Because the entire surface of the harmonized Modified Fullerene is enveloped in a Θ cloud 84 means that when viewed from the outside the harmonized Modified Fullerene will appear as one body mass with equal mass distribution in space.

We characterized the starting Modified Fullerene and the harmonized Modified Fullerene ($[C_{60}(OH)_{10-36}]^{\Phi/\phi}$) as follows: (1) starting substance $C_{60}(OH)_{10-36}$ with NMR ($^1$H NMR Bruker AC 250 E, 250 MHz and $^{13}$C NMR 62.9 MHz), IR (Perkin Elmer 457, FTIR Bomem MB100 FT), UV/Vis Perkin-Elmer series λ, ESR (Bruker ESR-300), TG (DuPont 1090 TA, TGA 951) and remanent magnetism (JR-5, with accuracy±3pT), (2) after harmonization $[C_{60}(OH)_{10-36}]^{\Phi/\phi}$ with $^{13}$C NMR and JR-5, (3) collagen in vitro with IR and FTIR before and after the harmonization procedure, (4) group of 50 mice which were induced by carcinoma before and after influence $[C_{60}(OH)_{10-36}]^{101\ /\phi}$, (5) group of 60 people with different skin problems including wrinkle, rashes, pigmentation, BCC, and skin cancer with documentation which include clinical pictures before and after treatment by $[C_{60}(OH)_{10-36}]^{\Phi/\phi}$, and (6) six human skin biopsies with characterization state of epiderm, basal membrane, collagen and elastin before and after treatment by $[C_{60}(OH)_{10-36}]^{\Phi/\phi}$.

Figure 7:
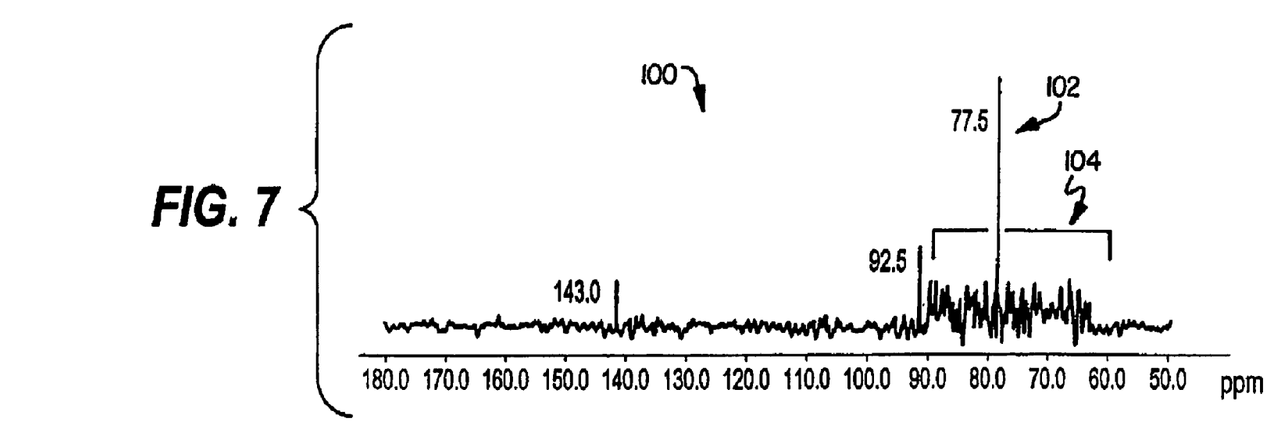
FIG. 7 is a $^{13}C$ NMR spectra for a hydroxyl modified fullerene $C_{60}(OH)_{24}$.

NMR is an effective characterization technique to distinguish a harmonized form of $[C_{60}(OH)_{10-36}]^{\Phi/\phi}$ from a non-harmonized form $C_{60}(OH)_{10-36}$. A non-harmonized form of $C_{60}(OH)_{10-36}$ will have a dominant peak from 72 ppm to 78 ppm representing the $C_{60}(OH)_{10-36}$ functional body (FIG. 7). Smaller peaks flank the dominant peak from 65.0 ppm to 95.0 ppm indicating that each atom of the $C_{60}$ is not equally covered by OH groups. The peak at 92.5 ppm indicates the presence of a catalysts such as NaBr, NaOH and $D_2O$. A small peak at 143.0 ppm indicates the presence of pure $C_{60}$ (C=C bonds).

FIG. 7 is a $^{13}$C NMR spectra 100 for $C_{60}(OH)_{24}$. A dominant peak 102 is located at 77.5 ppm flanked on both downfield and upfield sides by numerous smaller peaks, collectively referred to as 104, from 65 ppm to about 90 ppm. The dominant peak 102 represents the chemical shift (δ) 77.5 ppm indicating a $C_{60}OH_{24}$ functional body. The numerous smaller peaks are from 65 ppm to about 90 ppm are representative of the $C_{60}OH$ functional group(s). Thus, it is clear that not all $C_{60}$ are equally surrounded by OH groups.

Figure 8:
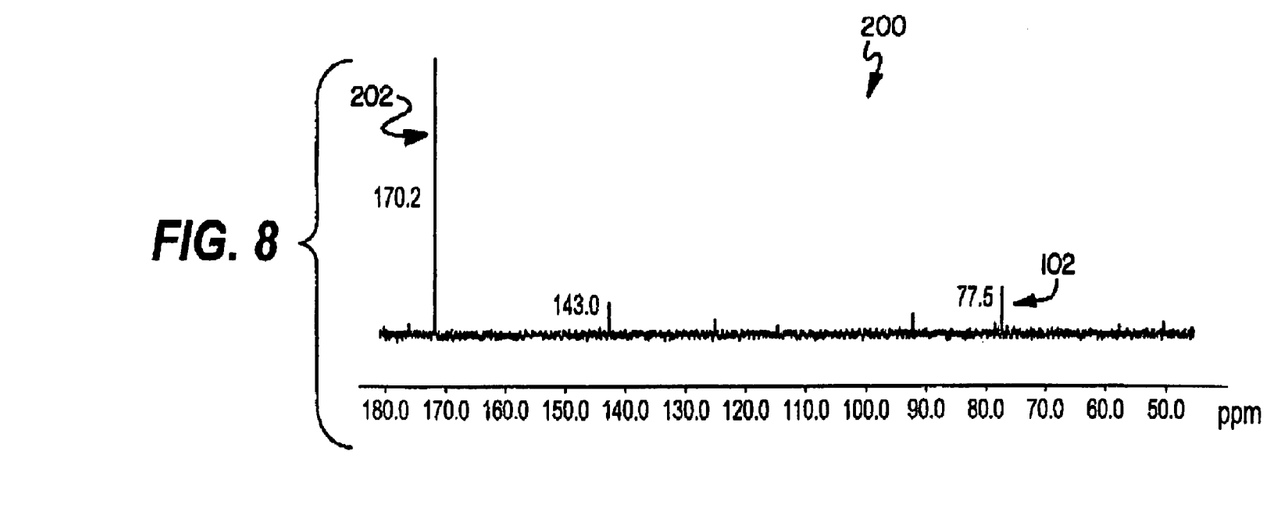
FIG. 8 is a $^{13}C$ NMR spectra for a harmonized, hydroxyl modified fullerene $[C_{60}(OH)_{10-36}]^{\Phi/\phi}$.

FIG. 8 shows a $^{13}$C NMR spectra for a harmonized, hydroxyl modified fullerene $[C_{60}(OH)_{24}]^{\Phi/\phi}$ 200 having a single dominant peak 202 at 170.2 ppm which indicates that each carbon atom of $C_{60}$ is equally covered by OH groups (notwithstanding the number of carbon atoms is 60, while number of OH groups is 24). Harmonized hydroxyl modified fullerene substance "appears" as a one body system. Peaks with smaller intensity on 77.5 ppm and 143.0 ppm indicate the presence of a small amount of non-harmonized hydroxyl modified fullerene substance and pure $C_{60}$ fullerenes, respectively. Thus, the harmonized, hydroxyl-modified fullerene shows all functional groups resonate at the same frequency, and, therefore appear as a body which has equal mass distribution in space.

The remanent magnetism of $C_{60}(OH)_{24}$ was measured before and after subjecting the $C_{60}(OH)_{24}$ to a harmonization procedure described above. The harmonized, hydroxyl modified fullerene $[C_{60}(OH)_{24}]^{\Phi/\phi}$ showed an increased magnetic field strength of about 4 nT.

Hydrated Harmonized Modified Fullerenes

FIG. 9 shows a harmonized Modified Fullerene 20 surrounded by water molecules 37 (hydrated harmonized Modified Fullerene). Three levels of hydrogen bonding are shown. The first level of hydrogen bonding 60 is between a hydrogen atom 62 of an OH group 26 and an oxygen atom 64 of an adjacent OH group 26 with each of these OH groups 26 covalently bonded to a carbon atom of the harmonized Modified Fullerene 20.

A second level of hydrogen bonding 70 occurs between an oxygen atom 64 of an OH group 26 of the harmonized Modified Fullerene 20 and a hydrogen atom 72 of a water molecule 37. The effects of the Θcloud 84 of temporally delocalized electrons of the harmonized Modified Fullerene acts as a template to cause the hydrogen bond lengths 70 between the harmonized Modified Fullerene 20 and the water molecules directly hydrogen bonding thereto, to obey the Fibonacci law. FIG. 5 shows a cluster of water molecules 25 having a covalent bond length 86 of 0.0957 nm and a hydrogen bond length 87 of 0.1548 nm wherein a ratio of the hydrogen bond length to the covalent bond length is 0.1548/0.0957=1.6175 which is 99.97% of the golden ratio of 1.61803. The intermolecular formula for this hydrated form of the harmonized Modified Fullerene will be designated as $[C_{60}(OH)_{24}]^{(\Phi/\phi)}.n(H_2O)$.

A third level of hydrogen bonding 80 occurs between hydrogen atoms 72 of water molecules 37 and oxygen atoms 82 of adjacent water molecules 72. The intermolecular formula for this two-layered hydrated structure will be designated as $\{[C_{60}(OH)_{24}]^{(\Phi/\phi)}.n(H_2O)\}m(H_2O)$.

The first level of hydrogen bonds is the strongest of the three and is 1.8 times stronger than the level three hydrogen bonds 80. The second level of hydrogen bonds 70 is the second strongest of the three levels and has a strength of 1.5 times that of level three hydrogen bonds 80. The hydrogen bonds of levels one and two provide the electron cloud 84 and produce an oscillatory magnetic field of 0.5 nT and causes water molecule surrounding the harmonized Modified Fullerene 20 to generate a magnetic field up to 4 nT.

A third hydrated form of the harmonized Modified Fullerene will include ions and will have the intermolecular formula of $\{[C_{60}(OH)_{24}]^{(\Phi/\phi)}.n(H_2O).p(Na^+, Cl^-, Mg^{2+}, Ca^{2+},$ and other ions$).m(H_2O)$. The ions can be present in an amount by weight of from about 0.01% to about 15%.

Cosmetic Products Based on $[C_{60}(OH)_{10-36}]^{\Phi/\phi}$

Cosmetic products containing the harmonized Modified Fullerene (HMF) can include from 0.1-25% by weight, more preferably from 0.2-15% and most preferably from 0.5-8% of the HMF with other substances commonly used in cosmetics to produce cosmetic compounds; moisturizing lotions, gels and oils; sun protection lotion, gels and oils; and other cosmetic products. Suitable delivery vehicles or components of such cosmetics can include, but are not limited to aqua purificate, propylene glycol, isopropyl isostearate, caprylic/capric triglyceride, *butyrospermum parkii* (Shea Butter), C12-20 acid PEG-8 ester, butyl methoxydibenzoylmethane, squalane, DEA-cetil phosphate, carbomer, *simmondisia chinensis* (Jojoba) seed oil, echinacea angustifolia extract, parfum, phenoxyethanol, methylparaben, propylparaben, ethylparaben, butylparaben, isobutylparaben, PEG-8, tocopherol, ascorbyl palmitate, ascorbic acid, citric acid, hydrolyzed serum protein, hydrolized yeast protein, pyridoxine, niacinamide, panthenol, allantoin, biotin, Vitamin C, sodium sydrocside, sodium, potassium, magnesium, zinc, cobalt, iron, chloride/sulfate, pentylene glycol, glycerin, propylene glycol, carbomer, sodium hydroxide, coenzyme Q10, vitamin A, vitamin E, proline, silver nanoparticulate, gold nanoparticulate, zinc oxide nanoparticulate, titanium dioxide nanoparticulate, active carbon micro- and nanoparticulate, and any type of icosohedral fullerenes.

The HMF cosmetic products are useful for numerous skin treatments including but not limited to, skin cancer, melanoma, non-melanoma, basal cell carcinoma, squamous cell carcinoma, merkle cell carcinoma, Bowen's disease, eccrine porocarcinoma, actinic keratosis, seborrheic keratosis, actinic porokeratosis, wounds, scars, inflammations, acne, rosacea, eczema, hyper-pigmentation, anti-aging prevention, wrinkle reduction, herpes, rashes, pimples, boils, sun-damage, solar lentigo, skin conditioning, skin rejuvenation, oily skin, stretch marks, cold sores, vein ulcers, incision scar healing, and other skin damage repairs, or conditions.

Example 1

Of a Topical Cream

The Phase A ingredients set forth in the table below were added to a tank in the order set forth in the table with mixing until the batch was uniform and smooth. The Phase B ingredient of a harmonized Modified Fullerene $[C_{60}(OH)_{24}]^{\Phi/\phi}$ (NHS-Best) was added to Phase A at 300 rpm until the mixture was uniform and smooth.

| PHASE | INGREDIENT | TRADE NAME | SUPPLIER | FUNCTION | WT. % |
|---|---|---|---|---|---|
| A | Water | DI water | | solvent/carrier | |
| A | polyacrylate-13, polyisobutene, polysorbate 20 | Sepiplus 400 | Seppic | emulsifier/viscosity modifier | 1-2 |
| A | pentylene glycol | Hydrolite-5 | Symrise | feel modifer | 5-10 |
| A | dimethicone | Dow Corning Q7-9120 | Dow Corning | emollient | 1-5 |
| A | Cyclopentasiloxane | Dow Corning 1501 fluid | Dow Corning | emollient | 5-35 |
| B | NA | NHS-Best | NA | active | 10-20 |

Example 2

Topical Cream

The ingredients set forth in the Table below were added together in the following order. Phase A ingredients were added to a first vessel and blended until uniform and lump free. Phase B ingredients were added to a second vessel and pasted. Add Phase C ingredients to a third vessel and add Phase B ingredients with high shear mixing. Add Phase D ingredients to Phases B/C and mix until all ingredients are dissolved. Slowly add Phase E ingredient $[C_{60}(OH)_{24}]^{\Phi/\phi}$ (NHS-Best) to Phase B/C/D and mix at or below 300 rpm until uniform. Slowly add and blend Phases B/C/D/E ingredients to Phase A in small increments and mix at or below 300 rpm. Continue mixing until the batch is uniform and smooth.

| PHASE | INGREDIENT | TRADE NAME | SUPPLIER | FUNCTION | WT. % |
|---|---|---|---|---|---|
| A | dimethicone; dimethicone/PEG-10/15 crosspolymer | KSG-210 | Shin Etsu | emulsifier | 1-10 |
| A | Bis-PEG/PPG-10/1 dimethicone | Abil EM 97 | Goldschmidt | emulsifier | 1-5 |
| A | dimethicone | Dow Corning 200 (100 cs) | Dow Corning | emollient | 5-20 |
| A | dimethicone | Dow Corning 200 (350 cs) | Dow Corning | emollient | 5-20 |
| A | dimethicone | Dow Corning 200 (1000 cs) | Dow Corning | emollient | 5-20 |
| B | pentylene glycol | Hydrolite-5 | Symise | feel modifier | 3-10 |
| B | *chondrus cripsus* (carrageenan) | Viscarin PC 389 | FMC | stabilizer | 0.1-1 |
| C | water | DI water | | solvent/carrier | 0-70 |
| D | sodium chloride | Sodium chloride | Morton | polarity modifier | 0.2-2 |
| E | NA | NHS-Best | | active | 10-20 |

Example 3

Topical Cream

The ingredients set forth in the Table below were added together in the following order. Phase A ingredients were added to a first vessel and blended until uniform and lump free. Phase B ingredients were added to a second vessel and mixed at 300 rpm or less until all solids dissolve. Add Phase B ingredients to Phase A while mixing at 300 rpm or slower until uniform.

| PHASE | INGREDIENT | TRADE NAME | SUPPLIER | FUNCTION | WT. % |
|---|---|---|---|---|---|
| A | dimethicone/vinyl dimethicone crosspolymer | USG-103 | Shin Etsu | solvent/carrier | 67-96 |
| A | dimethicone; dimethicone/PEG-10/15 crosspolymer | KSG-210 | Shin Etsu | emulsifier | 1-10 |
| A | bisabolol | Alpha Bisabolol Natural | Symise | anti-inflammatory | 0.01-0.5 |
| B | | NHS- Best | | active | 3-20 |
| B | sodium chloride | sodium chloride | Morton | polarity modifier | 0.1-1 |
| B | 1,2 hexanediol; caprylyl glycol | Symdiol 68 | Symise | preservative | 0.5-1.5 |

A Mother Tincture for Homeopathy Pharmaceuticals

Five published clinical outcome studies in homeopathy focus on diverse medical conditions: headache, acute otitis media, attention-deficit hyperactivity disorder (ADHD) in children, respiratory tract and ear complaints, including allergies, and male infertility (Muccari-Tomaioli, 2001, Frei, 2001a, Frei, 2001b, Riley, 2001, Gerhard, 2002) conclude in favor of the clinical effectiveness of homeopathy. The World Health Organization (WHO) is favorably disposed to homeopathy in spite of the resistance of medical doctors. However, in basic research, there are some contradictory results, but a recent experimental results about quantum property of hydrogen bonding indicate that the right homeopathy pharmaceuticals may have beneficial effects. Our invention is a mother of tincture product including HMF in a suitable carrier an in an amount by weight of from 0.6 mg/cm$^3$ to 14 mg/cm$^3$.

The present invention also provides a homeopathic composition having a harmonized form of a hydroxyl modified fullerene having a molecular formula of $C_{60}(OH)xH_y\forall_z$ (where x is from 10 to 36, and y is from 0 to 24 and z is from 0 to 12) for homeopathic pharmacy in concentration from $10^{-4}$ to $10^{-20000}$, or according to centesimal potency from 2cH to 10M.

NHS Stabilized Vitamin C

The harmonized form of $[C_{60}(OH)_{10-36}]^{\Phi/\phi}$ has been shown to be an effective stabilizing agent or preservative for increasing the shelf life of Vitamin C in an aqueous solution. It is contemplated that the shelf life of other environmentally delicate compounds could be increased with the use of the harmonized form of $[C_{60}(OH)_{10-36}]^{\Phi/\phi}$ either as a component in a solution or as an additive to a dry or semi-liquid dosage form. Environmentally delicate compounds can include those compounds that have a therapeutic of cosmetic effect. The compounds are typically in a composition suitable for delivery in vivo by an administrative route such as parenteral, oral, ophthalmic, topical, buccal, transdermal or the like.

Shelf-life studies were conducted on six aqueous solutions containing Vitamin C (L-ascorbic acid). The samples contain the contents as set forth in the Table below. Each of the samples were tested to determine the percentage of active Vitamin C remained in the sample after 28 days, 30 days and after being subjected to a heat treatment designed to simulate the sample had been stored for 120 days. Vitamin C activities were measured by: (1) HPLC (High-performance liquid chromatography) method using peak difference on 254 nm (retention time was 10.5 min, absorption maxima was on 244.5 nm based on Waters 996 photodiode array detector), and (2) time-dependent UV-vis absorption based on AA (L-ascorbic acid)-DHA (dehydroascorbic) acid. Initial AA peak (active vitC) was on 264 nm, while DHA peak (non-active vitC) was on 253 nm. Peak decreasing on 264 nm indicates the oxidation AA (when AA is oxidized to DHA the band shifted to lower wavelength at 253 nm)

Sample 1 results show that an 8.3% by weight solution of Vitamin C had only 0.12% active Vitamin C remaining after 28 days. Sample 2 results show that a 7.5% solution of Vitamin C had 18.2% of active Vitamin C remaining after 28 days. However, Sample 3 results show that when the harmonized form of $[C_{60}(OH)_{33}]^{\Phi/\phi}$ with 7.5% Vitamin C, 75.4% of the Vitamin C remained active after 28 days. Sample 4 results show that a 3.1% by weight solution of Vitamin C with the harmonized form of $[C_{60}(OH)_{33}]^{\Phi/\phi}$ 84.8% of the Vitamin C remained active after 28 days. When EDTA was added to a 3.1% by weight solution of Vitamin C along with the harmonized form of $[C_{60}(OH)_{33}]^{\Phi/\phi}$, Sample 5 results shows that 95.4% of Vitamin C remained after 28 days. Finally, Sample 6 results showed that adding EDTA alone, without adding the harmonized form of $[C_{60}(OH)_{33}]^{\Phi/\phi}$, to a 3.1% by weight Vitamin C solution had 2.3% active Vitamin C after 28 days.

Accordingly, the harmonized form of $[C_{60}(OH)_{33}]^{\Phi/\phi}$ is an effective preservative for Vitamin C in an aqueous solution.

Each of the samples was also tested by UV-vis spectrophotometer at the beginning (blind probe) and after 30 days to determine the capacity for the sample to scavenge radicals (Radical Scavenger Capacity). This test was conducted using 1,1-diphenil-2-picrylhydrazyl (DPPH). Samples were made in 18 different concentrations (from 2.5 μL to 200 μL substance in 10 mL 95% ethanol). For each sample a blind probe was done. The activity of samples was identified by the absorbance change occurring at 517 nm. RSC (Radical Scavenger Capacity) is equal to $IC_{50}$, which represent concentration of antioxidants when 50% of DPPH* radicals are scavenged ($IC_{50}$=50% RSC).

| Sample No. | Contents | Components in sample | After 28 days | After 30 days | Heat treatment Equivalence to 120 days | Normalized Radical Scavenger Capacity (RSC) |
|---|---|---|---|---|---|---|
| 1 | 8.3% VitC in water | 1.66 mg - vitC<br>18.34 mg - water | 0.12% | 0.10% | <0.01% | 1 |
| 2 | 7.5% VitC in $C_{60}(OH)_{10-36}$ (not harmonized) | 1.50 mg - vitC<br>18.50 mg - $C_{60}(OH)x$ | 18.2% | 18.1% | 2.2% | 39 |
| 3 | 7.5% VitC in $[C_{60}(OH)_{10-36}]^{\Phi/\phi}$ | 1.50 mg - vitC<br>18.50 mg -$[C_{60}(OH)x]^{\Phi/\phi}$ | 75.4% | 75.3% | 71.2% | 43 |
| 4 | 3.1% VitC in $[C_{60}(OH)_{10-36}]^{\Phi/\phi}$ | 0.62 mg - vitC<br>19.38 mg-$[C_{60}(OH)x]^{\Phi/\phi}$ | 84.8% | 84.7% | 82% | 81 |
| 5 | 3.1% VitC in $[C_{60}(OH)_{10-36}]^{\Phi/\phi}$ + EDTA | 0.62 mg - vitC<br>16.50 mg-$[C_{60}(OH)x]^{\Phi/\phi}$<br>2.88 mg - EDTA | 95.4% | 95.5% | 95.2% | 82 |
| 6 | 3.1% VitC in EDTA | 0.31 mg - vitC<br>9.69 mg -EDTA | 2.3% | 2.2% | 0.05% | 6 |

Based on these results for Vitamin C it is contemplated that other environmentally delicate substances could be stabilized by adding an effective amount of a harmonized form of $[C_{60}(OH)_{10-36}]^{\Phi/\phi}$. Other therapeutic substances include vitamins, hormones, peptides, polypeptides, pharmaceutically active compounds, proteins, minerals, electrolytes and others.

Example of an anti-inflammatory containing, harmonized modified fullerene topical cream The ingredients set forth in the Table below were added together in the following order. Phase A ingredient, water, was added to a first vessel. Phase B ingredients were added to a second vessel and pasted. Add Phase C ingredients to Phase B ingredients with mixing and heat to 70° to 75°. Add Phase D ingredients to Phases B/C, heat to 70° to 75°, and mix until all solids melt. Add Phase B/C/D ingredients to the water and mix until uniform and cool to 35°. Add Phase E ingredient $[C_{60}(OH)_{24}]^{\Phi/\phi}$ (NHS-Best) to Phase A/B/C/D and mix at or below 300 rpm until uniform.

| PHASE | INGREDIENT | TRADE NAME | SUPPLIER | FUNCTION | WT. % |
|---|---|---|---|---|---|
| A | water | DI water | | solvent/carrier | 29-83 |
| B | propanediol | Zemea | DuPont/Tate & Lyle | wetting agent | 0.2-3 |
| B | xantham gum | Keltrol CG | C.P. Kelco | emulsion stabilizer | 0.1-1 |
| C | glycerin | Glycerin | | feel modifier | 0.2-5 |

-continued

| PHASE | INGREDIENT | TRADE NAME | SUPPLIER | FUNCTION | WT. % |
|---|---|---|---|---|---|
| C | tetrasodium EDTA | Versene 220 | Dow Chemicals | chelating agent | 0.02-0.1 |
| D | cetearyl alcohol; ceteareth-20 | Cosmowax P | Croda | emulsifier | 2-8 |
| D | caprylic/carpic triglyceride | Captex 300 | Abitec | emollient | 3-15 |
| D | butyrospermum Parkii (Shea butter) | Shea Butter | Classic Distributing | emollient | 3-15 |
| E | bisabolol | Alpha bisabolol | Symise | anti-inflammatory | 0.05-0.5 |
| E | 1,2 hexanediol, caprylyl glycol | Symdiol 68 | Symise | preservative | 0.5-1.5 |
| E | butylene glycol | 1,3 butylene glycol | Univar | feel modifier | 2-6 |
| E | NA | NHS-Best | | active | 6-15 |

From the foregoing it will be observed that numerous variations and modifications may be effected without departing from the spirit and scope of the invention. It is to be understood that no limitation with respect to the specific inventions disclosed herein is intended or should be inferred. It is, of course, intended to cover by the appended claims all such modifications as fall within the scope of the claims.

What is claimed is:

1. A composition of matter comprising a harmonized ($\Phi/\phi$) form of a hydroxyl modified fullerene having a molecular formula of $C_{60}(OH)_xH_y\forall_z$ (where x is from 10 to 36, and y is from 0 to 24 and z is from 0 to 12 the composition of matter having a $^{13}C$ NMR spectra having a dominant peak at 170.2 ppm.

2. The composition of matter of claim 1 ($[C_{60}(OH)xH_y\forall_z]^{(\Phi/\phi)}$) wherein the composition has a remanent magnetism differing from a remanent magnetism of a non-harmonized $C_{60}(OH)xH_y\forall_z$ (where x is from 10 to 36, and y is from 0 to 24 and z is from 0 to 12) by about 4 nT.

3. The composition of matter of claim 1 having a molecular formula of $[C_{60}(OH)_{24}]^{(\Phi/\phi)}$.

4. The composition of matter of claim 1 having a first hydrated form with an intermolecular formula $[C_{60}(OH)_{24}]^{(\Phi/\phi)}.n(H_2O)$.

5. The composition of matter of claim 1 having a second hydrated form with an intermolecular formula $\{[C_{60}(OH)_{24}]^{(\Phi/\phi)}.n(H_2O)\}m(H_2O)$.

6. The composition of matter of claim 1 having a molecular formula of $[C_{60}(OH)_{24}]^{(\Phi/\phi)}$ and intermolecular formula $\{[C_{60}(OH)_{24}]^{(\Phi/\phi)}.n(H_2O)\}$ p($Na^+$, $Cl^-$, $Mg^{2+}$, $Ca^{2+}$, and other ions), when n-water molecules are in one, two or three layers, and p– ions in different concentration from 0.01% to 15%.

7. The composition of matter of claim 1 having an intermolecular formula $\{[C_{60}(OH)_{24}]^{(\Phi/\phi)}.n(H_2O).p(Na^+, Cl^-, Mg^{2+}, Ca^{2+},$ and other ions).m($H_2O$).

8. The composition of matter of claim 1 is not cytotoxic when measured by an Ames test.

9. A biologically effective composition comprising:
a harmonized form of a hydroxyl modified fullerene having a molecular formula of $C_{60}(OH)xH_y\forall_z$ (where x is from 10 to 36, and y is from 0 to 24 and z is from 0 to 12) from 1 to 20% by weight of the composition; and
a carrier in an amount by weight of from 80% to 99% by weight of the composition.

10. The composition of claim 9 wherein the carrier is selected from the group consisting of aqua purificate, propylene glycol, isopropyl isostearate, caprylic/capric triglyceride, butyrospermum parkii (Shea Butter), C12-20 acid PEG-8 ester, butyl methoxydibenzoylmethane, squalane, DEA-cetil phosphate, carbomer, simmondisia chinensis (Jojoba) seed oil, echinacea angustifolia extract, parfum, phenoxyethanol, methylparaben, propylparaben, ethylparaben, butylparaben, isobutylparaben, PEG-8, tocopherol, ascorbyl palmitate, ascorbic acid, citric acid, hydrolyzed serum protein, hydrolized yeast protein, pyridoxine, niacinamide, panthenol, allantoin, biotin, Vitamin C, Vitamin E, Vitamin A, sodium sydrocside, sodium, potassium, magnesium, zinc, cobalt, iron, chloride/sulfate, pentylene glycol, glycerin, propylene glycol, carbomer, and sodium hydroxide.

11. The composition of claim 9 wherein the carrier is suitable for pharmaceutical, medical or cosmetic usage.

12. The composition of claim 9 further comprising a therapeutic substance.

13. The composition of claim 11 wherein the therapeutic substance is selected from the group consisting of vitamins, hormones, peptides, polypeptides, pharmaceutically active compounds, proteins, minerals, electrolytes.

14. The composition of claim 12 wherein the therapeutic substance is Vitamin C.

15. An aqueous solution containing Vitamin C and having an enhanced shelf life comprising:
from 1%-7.5% by weight of Vitamin C in water; and
from 10%-25.5% by weight of harmonized, hydroxyl modified fullerene having a molecular formula of $[C_{60}(OH)xH_y\forall_z]^{(\Phi/\phi}$ (where x is from 10 to 36, and y is from 0 to 24 and z is from 0 to 12).

16. The solution of claim 15 further comprising an additive selected from the group of coenzyme Q10, vitamin A, vitamin E, proline, silver nanoparticulate, gold nanoparticulate, zinc oxide nanoparticulate, titanium dioxide nanoparticulate, active carbon micro- and nanoparticulate, and any type of icosohedral fullerenes.

17. The solution of claim 16 wherein the additive is EDTA.

18. The solution of claim 17 wherein the solution contains in excess of 70% by weight of active Vitamin C after 28 days of storage.

19. A biologically effective composition comprising:
   a harmonized form of a hydroxyl modified fullerene having a molecular formula of $C_{60}(OH)xH_y\forall_z$ (where x is from 10 to 36, and y is from 0 to 24 and z is from 0 to 12) for homeopathic pharmacy in concentration from $10^{-4}$ to $10^{-20000}$, or according to centesimal potency from 2 cH to 10 M.

* * * * *